United States Patent [19]

Houwen et al.

[11] Patent Number: 5,675,760

[45] Date of Patent: Oct. 7, 1997

[54] APPARATUS AND METHOD FOR DISPLAYING NORMALIZED CLINICAL TEST DATA

[75] Inventors: Berend Houwen, Redlands, Calif.; Shigeo Kanamori, Miki; Kaoru Asano, Kobe, both of Japan

[73] Assignee: Toa Medical Electronics Co., Ltd., Hyogo-Ken, Japan

[21] Appl. No.: 303,205

[22] Filed: Sep. 8, 1994

[30] Foreign Application Priority Data

Sep. 10, 1993 [JP] Japan ................... 5-225745

[51] Int. Cl.⁶ .................................. G06T 11/00
[52] U.S. Cl. ........................................ 395/140
[58] Field of Search ............... 395/140, 155–161, 395/326, 333–335; 364/413.01–413.12

[56] References Cited

U.S. PATENT DOCUMENTS 4,920,498  4/1990  Kaneko ................. 395/140 X

FOREIGN PATENT DOCUMENTS 2-304362  12/1990  Japan .
5-26533   7/1993   Japan .

OTHER PUBLICATIONS

Marshall "Graphical Methods" 1921 pp. 60, 61, 64, 65.
Schecke T. et al., "Knowledge-based decision support for patient monitoring in cardioanesthesia", *International Journal of Clinical Monitoring and Computing*, 1992, Netherlands, vol. 9, No. 1, ISSN 0167–9945, pp. 1–11.
Bankman, I. N., Tsitlik J.E., Proceedings of the Annual Symposium on Computer Based Medical Syste, Baltimore, May 12–14, 1991, Conf. 4, May 12, 1991, pp. 88–93; Nevo I. et al., "A New Patients' Status Indicator to Facilitate Decision Making in Anesthesia".

*Primary Examiner*—Almis R. Jankus

[57] ABSTRACT

A calculator selects desired data out of a set of data obtained by analyzing a sample, such as blood or urine, and normalizes the selected data with respect to a predetermined level. The normalized values obtained by the calculator may be displayed as values and/or graphs. The graphical display may show a partition line set according to the experiences of the laboratory, so the graph may be quickly understood.

21 Claims, 5 Drawing Sheets

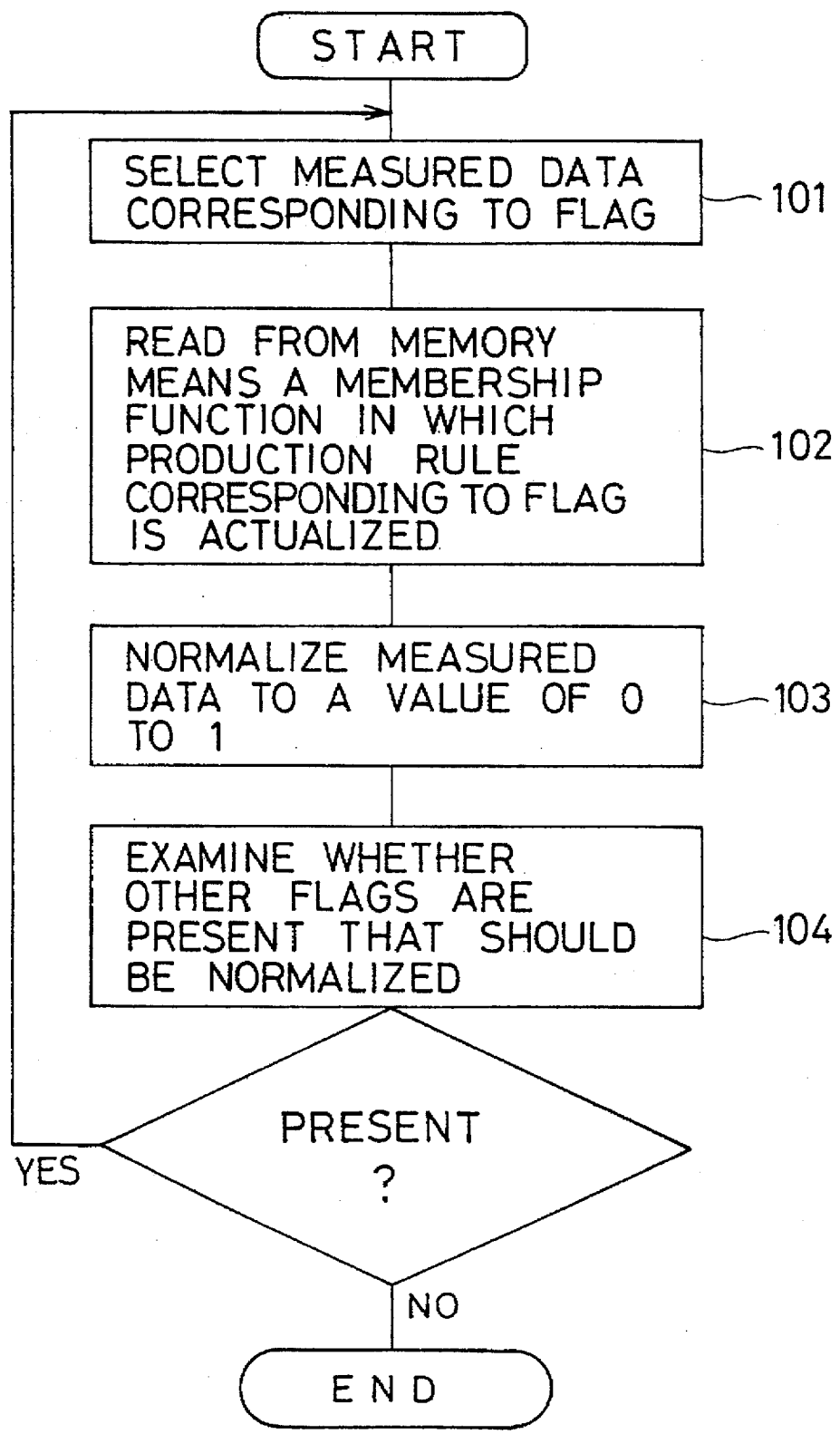

MEMBERSHIP FUNCTION CORRESPONDING TO FRAME 1

MEMBERSHIP FUNCTION CORRESPONDING TO FRAME 2

FIG. 5

DISPLAY SCREEN OF FLAGS

| QUANTITATIVE FLAGS | | | | | | |
|---|---|---|---|---|---|---|
| WBC ABN 0.23 | BLAST 0.04 | IMM GRAN 0.12 | L-SHIFT 0.19 | ATYP LYM 0.21 | NRBC 0.07 | |
| RBC ABN 0.19 | DIMORPH 0.11 | RBC AGG 0.14 | TURB/HGB 0.80 | IRON DEF 0.22 | HGB DEF 0.24 | FRAG 0.17 |
| PLT ABN 0.29 | LARGE PLT 0.42 | SMALL PLT 0.28 | PLT CL 0.34 | RBC/PLT 0.36 | | |

APPARATUS AND METHOD FOR DISPLAYING NORMALIZED CLINICAL TEST DATA

BACKGROUND OF THE INVENTION

1. Field of the Invention

The present invention relates to a display apparatus for displaying clinical test results obtained by a sample analyzer, and more particularly to a clinical test result display apparatus for displaying test results such as information that can be used for diagnosis (for example, information on hematosis or abnormal conditions).

2. Description of the Related Art

Conventional sample analyzers include, for example, a blood cell analyzer which counts the number of cells in blood such as white blood cells (WBC), red blood cells (RBC), and platelets (PLT) by detecting differences between such cells in electric or optical properties.

Such sample analyzer converts a variety of measured data into numerical data or particle distribution charts (one or two dimensional distribution) to which some additional information (flags or messages) is added and displayed on a screen of the analyzer in order to help clinical diagnosis.

A method for analyzing blood data is proposed which involves judging numerical data such as the number of white blood cells and red blood cells and data on particle distribution by quantitatively comparing actually measured data (object) and preliminarily set criteria (thresholds) for each message (for example, RBC Intf., Blasts and so on) with a processor having a CPU thereby displaying a message that may contain abnormal conditions based on the result of judgment (see Japanese Published Unexamined Patent Application No. HEI 2-304362).

A method using a bar graph is available as one of general methods for displaying measured data in such a manner that an operator can easily understand what such data actually means. For example, an automatic analyzer is known, which calculates a residual amount of a sample or reagent and processes it as a bar graph, while a color is added to the bar graph and displayed when the residual amount is found to be lower than a supply limit. (see Japanese Published Unexamined Utility Model Application No. HEI-5-26533).

However, in accordance with the method described in Japanese Published Unexamined Patent Application No. HEI 2-304362, a judgment is passed on each message by quantitatively comparing measured data with a preset threshold. Such judgment based on the quantitative Comparison involves irrationalities such that the test result is reversed because of a fine variation in the measured data thereby failing to provide messages.

That is to say, when measured data obtained by analyzing the sample is compared with the threshold to express the measured data in a binary value to display test result information (flags or messages), the following problems are encountered.

(1) No gray scale display of the flag or message can be given. In other words, no certainty of the flag or message can be displayed.

(2) It is not certain whether the same flag or message can be reproduced in the same sample.

Additionally, the analyzer described in Japanese Published Unexamined Utility Model No. HEI 5-26533 can accurately control the supply condition of a sample or a reagent by displaying a residual amount of the blood sample or the reagent in each container with a bar graph and displaying the supply limit in different colors so that the residual amount can be confirmed at a glance. However, when such analyzer is applied to a display for clinical tests, the measured items are not limited to one but to a plurality of items in a general analysis and judgment of samples. One measurement item is not sufficient in the control of clinical tests.

Furthermore, it is indispensable to obtain measured data such as counting values and particle distribution chart for the control of the clinical test results. In addition, it is important to obtain in an understandable manner information on whether an additional test is required, information on whether or not a different test (thorough test) is required, or information on how such data can be used in the diagnosis of diseases.

However, the conventional clinical test system has a fixed judgment logic and process. In other words, since such clinical test system is under the control of manufacturers, the system rejects the adoption of a reference for judging actually measured data for each institution based on experience and knowledge of specialists even when the ratio at which abnormal samples occupy differs and the ratio at which such samples are allowed to undergo reexamination differs from one institution (such as a hospital and clinical laboratory) to another.

The present invention has been made to overcome the aforementioned problems.

SUMMARY OF THE INVENTION

The present invention provides a clinical test result display apparatus comprising calculating means for selecting desired data out of measured data obtained by analyzing a sample and normalizing the selected data with respect to a predetermined level and display means for displaying as a value and/or a graph at least one normalized value obtained by the calculating means.

BRIEF DESCRIPTION OF THE DRAWINGS

FIG. 2 is a flowchart showing the procedure of a data management system of the present invention.

FIG. 5 is an explanatory view showing one embodiment of a display screen of the test result information (a flag).

DETAILED DESCRIPTION OF THE PREFERRED EMBODIMENTS

Figure 1:
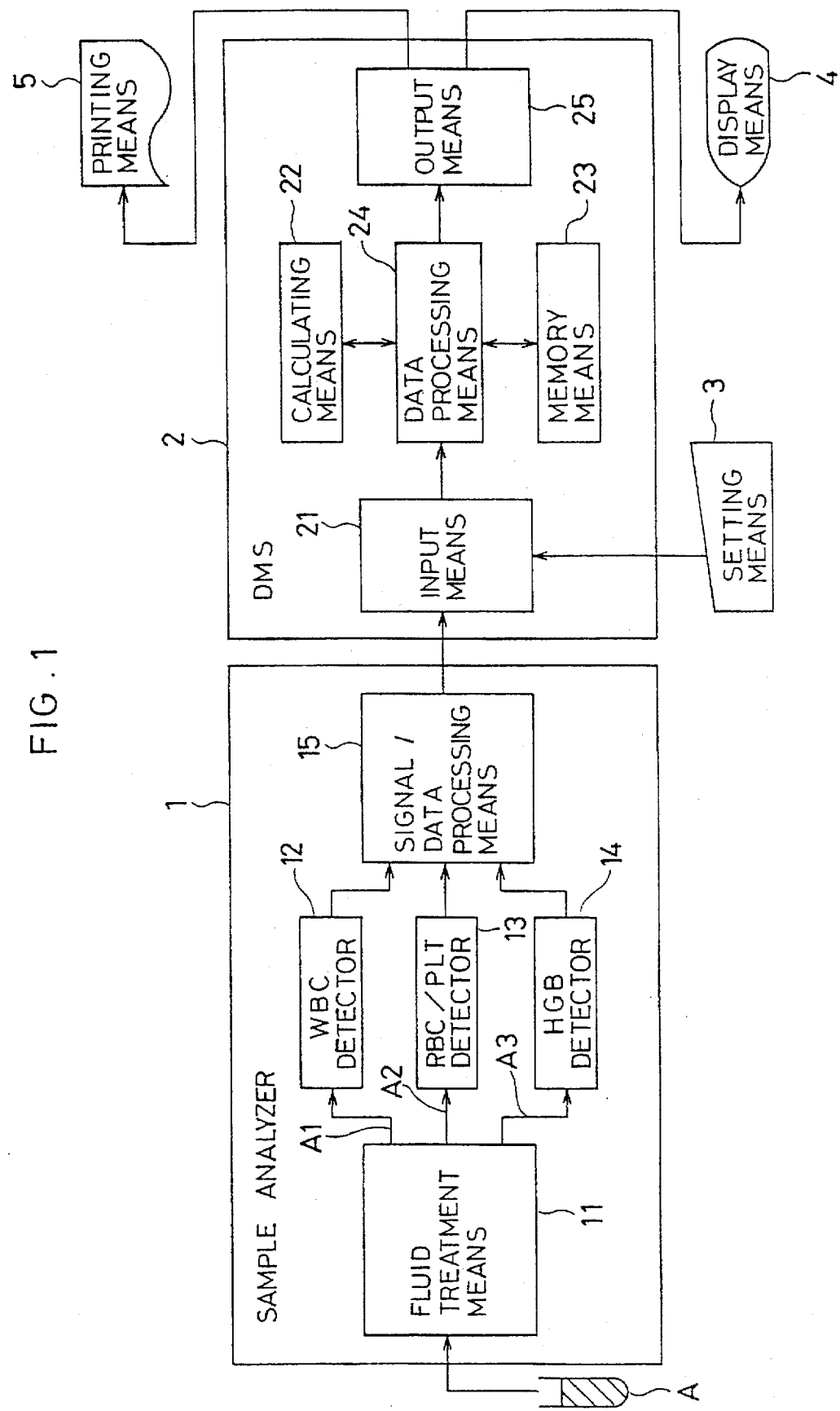
FIG. 1 is a block diagram showing one embodiment in which the present invention is applied to a clinical test apparatus.

In accordance with the present invention, a microcomputer system comprising a CPU, a ROM, a RAM and an I/O port is preferably used as the calculating means. In particular, a computer is used which comprises a fuzzy reasoning or a neural network as a microcomputer system normalizing measured data with respect to a predetermined level.

Examples of the display means include a color CRT (cathode ray tube) display, a color LCD (liquid crystal display) or an EL display having a character generator that can display figure data, character data and graph data. In addition, the display means provides means for converting normalized measured data into display data represented in a box-like graph attached with a threshold.

In addition, the clinical test result display apparatus according to the present invention is either connected to the outside of a blood cell analyzer, a serum analyzer, a urine analyzer, a coagulation analyzer, an immunology analyzer or the like or incorporated in such analyzers.

In accordance with the present invention, the calculating means selects desired data out of measured data obtained in the analysis of a sample and normalizes selected data with respect to a predetermined reference to display the normalized data as a value and/or a graph.

The aforementioned predetermined reference refers to a judgment rule or a membership function in a fuzzy reasoning, weights of network connections and a sigmoid function in neural network, or a predetermined function in function operation function.

The aforementioned threshold refers to a value voluntarily set based on the ratio at which abnormal samples occupy in all the samples and the reexamination ratio that can be permitted. The value can be set within the range of 0 to 1.

Preferably, the aforementioned display means comprises a display function for displaying measured data in a box-like graph attached with a threshold.

More preferably, the display means displays normalized data with an area of the box-like graph having a maximum value of 1 for each test result information and displays the threshold thereof as a partition line on the box-like graph.

Even more preferably, the display means displays normalized data that exceeds the threshold by changing the color of the character display of the test result information corresponding to the normalized data and the display color of the box-like graph.

The aforementioned calculating means comprises a computer which provides a fuzzy reasoning, a neural network, or a predetermined function.

The calculating means normalizes measured data with respect to a predetermined value into a value ranging from 0 to 1 with the fuzzy reasoning, the neural network or the function operation.

The present invention will be detailed in conjunction with the accompanying drawings, but the invention is not limited to them.

Besides, the present invention is preferable as a clinical test result display connected to, for example, a blood cell analyzer, a serum analyzer, a urine analyzer or the like. An explanation is given that each constituent element provides a display function of normal clinical test result data except for accomplishing "Function of Displaying Box-Like Graph Providing Threshold Value of the Clinical Test Result Information".

FIG. 1 is a block diagram showing one embodiment in which the present invention is applied to the clinical test apparatus. Referring to FIG. 1, reference numeral I designates a sample analyzer for analyzing a sample A such as blood, urine or the like, and 2 a data management system (DMS) for data processing such as receipt of measured data, analysis, normalization and judgment of measured data, and preparation of messages. DMS2 refers to a computer providing a microcomputer which comprises a CPU, a ROM, a RAM and an I/O port, and an input and output device. The function of the DMS2 constitutes a characteristic of the present invention.

Reference numeral 3 designates setting means for entering data, and such devices as a keyboard, a pen input tablet, a mouse or the like are used.

Reference numeral 4 designates display means for displaying data on a screen, and such displays as color LCD's and color CRT's providing means for converting measured data normalized by the DMS2 into box-like graph data having a threshold.

Reference numeral 5 designates printing means for printing and outputting data, and color printers such as ink jet printers, laser printers or the like are used as such printing means.

The sample analyzer 1 comprises fluid treatment means 11 for preparing test liquids A1, A2 and A3 by pretreatment such as sampling, diluting, lysing and staining of a sample A for the analysis thereof, a WBC detector 12, a RBC/PLT detector 13 and a HGB detector 14 for measuring the test liquids A1, A2 and A3, and a signal and data processing means 15 for converting and processing measurement signal obtained by the detectors 12, 13 and 14 into a desired type of data (such as numerical data and particle distribution data on WBC and numerical data and particle distribution data on RBC and numerical data on HGB).

The DMS2 comprises input means 21 for taking numerical data and particle distribution data output from signal and data processing means 15, memory means 23 for storing not only input measured data but also a production rule, a membership function, a constant, a fuzzy operation program, a data processing program, test result information (flags or messages), calculating means 22 for normalizing data by using at least one measured data, data processing means 24 for processing each type of data by the data processing program, and output means 25 for outputting processed data to the display means 4 or to the printing means 5.

Furthermore, as the calculating means 22 for normalizing the measured data with respect to the predetermined reference, a personal computer constituting a neural network instead of the fuzzy reasoning may be used. Otherwise, normalization calculation using a predetermined function may be performed.

Still furthermore, as memory means 23, a memory may be particularly used which comprises a RAM temporarily storing measured data, a ROM preliminarily storing a fuzzy reasoning program, a data processing program, and measurement information, a floppy disk drive and a hard disk drive.

Examples of measured data obtained by the blood cell analyzer include eight items of fundamental data such as the white blood cell count (WBC) the red blood cell count (RBC), the hemoglobin concentration (HGB), hematocrit (HCT), mean corpuscular volume (MCV), mean corpuscular hemoglobin (MCH), a mean corpuscular hemoglobin concentration (MCHC), and the platelet count (PLT); five differential data on white blood cells such as the number of neutrophils (NEUT#) and the ratio of neutrophils (NEUT%), the number of lymphocytes (LYMPH#) and the ratio of lymphocyte (LYMPH%), the number of monocytes (MONO#) and the ratio of monocytes (MONO%), the number of eosinophils (EO#) and the ratio of eosinophils (EO%), and the number of basophils (BASO#) and the ratio of basophils (BASO%); particle analysis data on red blood cell distribution width-SD (RDW-SD), red blood cell distribution width-CV (RDW-CV), the platelet distribution width-SD (PDW-SD), mean platelet volume (MPV), the ratio of large platelet (P-LCR); and data on the distribution of each particle such as white blood cells, red blood cells and platelets.

There will be described hereinbelow on a case in which these items of measured data are used to obtain normalized data normalized by the calculating means 22 for each item of test result information (flag or message) and 18 items of test result information are displayed together with a box-like graph on the normalized data.

Eighteen items of test result information (flags or messages) are described below.

WBC ABN; WBC Abnormal Distribution

This flag indicates that the WBC particle distribution is abnormal (POSITIVE Morph.) or the analysis result is abnormal (POSITIVE Count).

BLAST; Blasts

This flag indicates that blasts might be present.

IMM GRAN; Immature Granulocytes

This flag indicates that immature granulocytes might be present.

L-SHIFT; Left shift

This flag indicates that the left shift might be present (neutrophils are relatively immature).

ATYP LYM; Atypical Lymphocytes

This flag indicates that atypical lymphocytes might be present.

NRBC; NRBC

This flag indicates that nucleared red blood cell might be present

RBC ABN; RBC Abnormal Distribution.

This flag indicates that RBC particle distribution is abnormal (POSITIVE Morph) or that the analysis result is abnormal (POSITIVE Count).

DIMORPH; RBC Dimorphic Population

This flag indicates that the RBC distribution is given as two dimorphic population (plurality of populations).

RBC AGG; RBC Agglutination

This flag indicates that RBC agglutination might be present.

TURB/HGB; Turbidity/HGB Interference

This flag indicates that the HBG value is interfered by hyperlipidermia or the like.

IRON DEF; Iron Deficiency

This flag indicates that iron deficiency might be present.

HGB DEF; HGB Defect

This flag indicates that hemoglobin defect might be present.

FRAG; Fragments

This flag indicates that fragment red blood cell might be present.

PLT ABN; PLT Abnormal Distribution

This flag indicates that PLT particle distribution is abnormal (POSITIVE Morph.) or that the analysis result is abnormal.

LARGE PLT; large PLT

This flag indicates that large platelets might be present.

SMALL PLT; small PLT

This flag indicates that small platelets might be present.

PLT CL; PLT Clumps

This indicates that platelet clumps might be present.

PBC/PLT Micro RBC/PLT Interference

This flag indicates that the PLT value might be affected by the contamination of small red blood cells.

Then, a case will be explained in which TURB/HGB is normalized. The normalization here refers to the determination of the scope in which a graph is determined by using a necessary data for each flag as a value in the scope ranging from a predetermined minimum value to a predetermined maximum value (for example 0 to 1). As such example, a case will be explained in which normalization is done using a fuzzy reasoning.

Incidentally, with respect to an application to a clinical test, reference can be made to an article entitled "Usefulness of Fuzzy Theory for the Processing of Border in Medical Information" published in the 6th Japanese Journal of Medical Electronics and Biological Engineering, Vol. 30, Suppl., 1992, Page 3 Special Autumn Issue (1992).

FIG. 2 is a flowchart showing a processing procedure of a data management system according to the present invention. The processing procedure shown in the flowchart of FIG. 2 will be explained in conjunction with FIG. 3(a) and 3(b).

At step 101, only MCHC is selected out of measured data from the memory means 23 in TURB/HGB.

At step 102, a membership function is read from the memory means 23 in which a production rule corresponding to TURB/HGB is actualized.

Rule 1 of the production rule provides that if MCHC is large, then the sample is TURB/HGB.

Figure 3A:
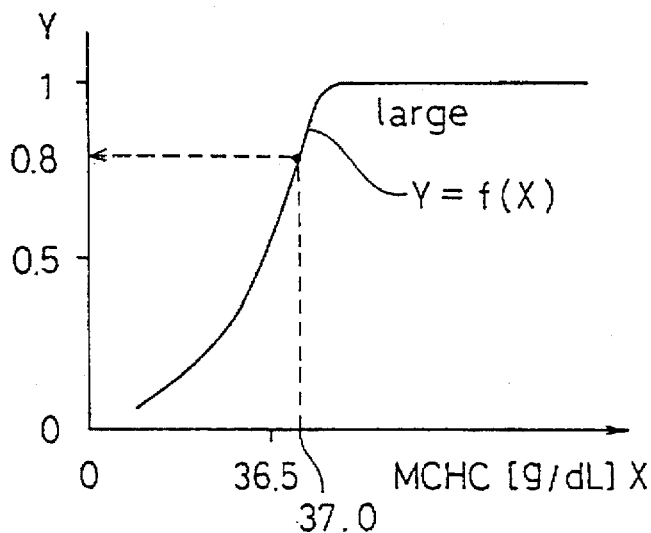
FIGS. 3(a) and 3(b) show respective embodiments for a membership function of the present invention.

FIG. 3 is a view illustrating one embodiment of a membership function according to the present invention. As shown in FIG. 3(a), a membership function of Y=f (X) is read from the memory means 23 and allocated.

At step 103, a value of the measured data is substituted into the allocated membership function to be normalized into a value of 0 to 1. In other words, normalized data of the TURB/HGB flag can be obtained by substituting a value of MCHC as X into the membership function of Y=f(X). The normalized data refers to a probability of TURB/HGB flag.

In this case, since MCHC assumes 37.0 [g/dL] as shown in FIG. 3(a), the normalized data is given as 0.80.

Step 104 is to examine whether there are other flags that should be normalized. If there are no other flags that should be normalized, data processing is terminated. When there are other flags that should be normalized, step returns to step 101. Steps 101 to 104 are repeated, and data processing is terminated.

Other flags can be normalized in the same manner by preparing a rule and a membership function suitable for the rule.

Here, a brief example is given in a case in which a plurality of data items $(X_1, X_2)$ are selected to obtain one normalized data item with respect to the flag Q from this plurality of data items.

Rule 2 provides that if ($X_1$ is small) and ($X_2$ is large), then Q.

Figure 3B:
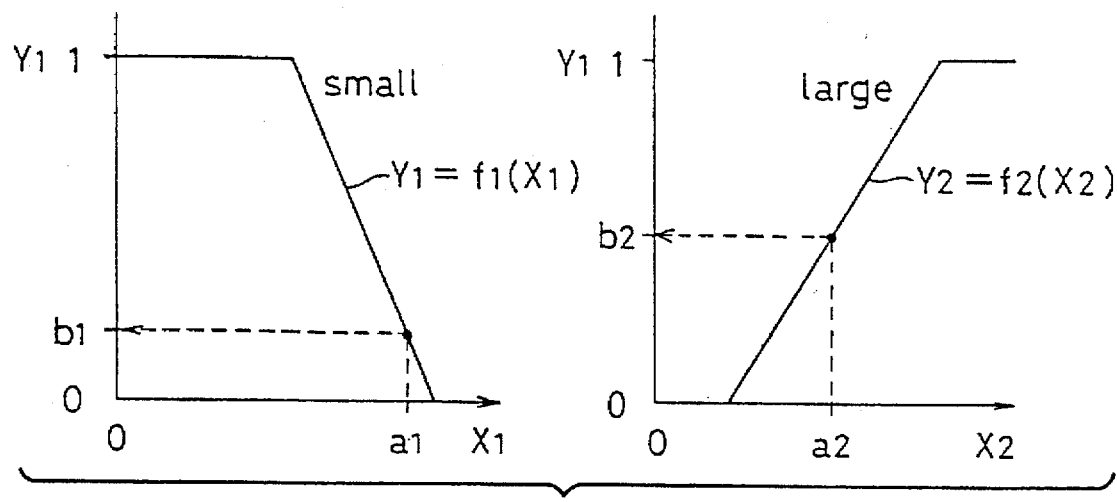

As shown in FIG. 3(b), as a membership function corresponding to rule 2. $Y_1=f_1 (X_1)$ and $Y_2=f_2 (X_2)$ Supposing that $Y_1=b_1$, $Y_2=b_2$ and $b_1<b_2$ were obtained by substituting $Y_1=f_1$ (X1) and $Y_2=f_2 (X_2)$ with $X_1=a_1$ and $X_2=a_2$ being given. The smaller value $b_2$ is given as normalized data of flag Q. (When the above rule 2 is connected with or, a larger value b2 is adopted.

Figure 4:
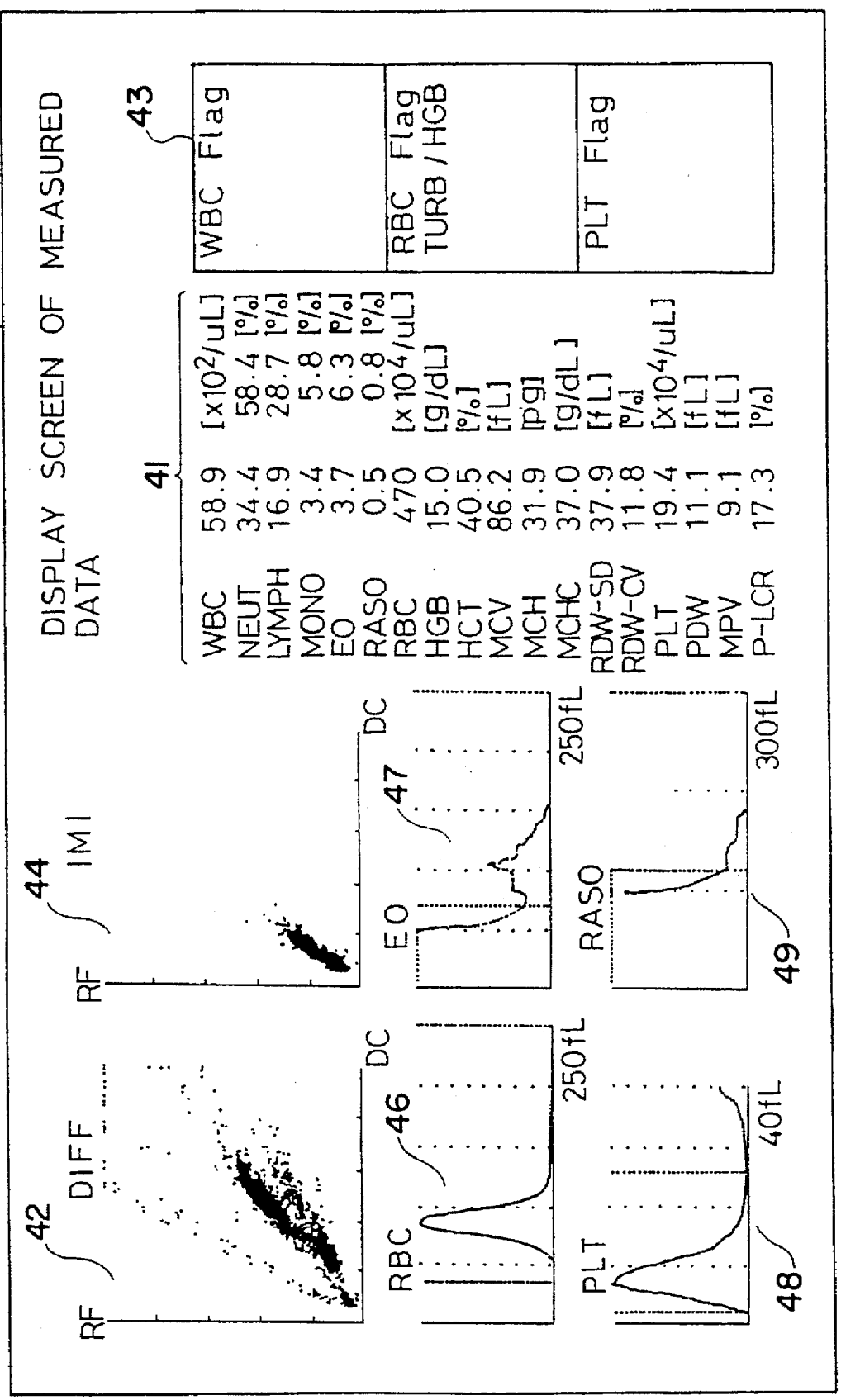
FIG. 4 is an explanatory view showing one embodiment of a display screen of measured data according to the present invention.

FIG. 4 is a view showing one display example of a display screen (40) of measured data according to the present invention. Referring to FIG. 4, numerals 42 and 44 designate a WBC scattergram (two parameter distribution), numeral 46 a single parameter particle distribution of RBC, numeral 48 a single parameter particle distribution of PLT (platelets), numeral 47 a single parameter particle distribution of EO (eosinophil), and numeral 49 a single parameter distribution of BASO's (basophiis), numeral 41 a measurement item and a numerical data corresponding to the measurement item, numeral 43 a test result information (flag). When normalized data exceeds a threshold, a flag is adjusted in correspondence to such state, for example, TURB/HGB is displayed, the fact that the HGB value might be interfered by the hiperlipidermia can be easily confirmed.

FIG. 5 is a view showing a display example of a display screen 50 for the test result information (flag) according to the present invention. Referring to FIG. 5, numeral 52 designates a WBC flag display region, numeral 54 a RBC flag display region, and numeral 56 a PLT flag display region.

For the visual representation of the probability of the flag (normalized data), a box-like graph is preferably represented by the length and the area. Box-like graphs include a rectangular bar graph, and circle graph. Here the graph is given as a rectangular box-like graph.

Besides, for an easy display of the threshold for judgment and a box-like graph representation, a display using a calibration and a partition line is preferable. Here a line segment display segmenting regions of the box-like graph is adopted with a partition line 55 added to both sides of the box-like graph.

Flag names 58 (WBC ABN, BLAST, IMM GRAN,- - -), normalized data displayed as a box-like graph and a threshold added to the boxlike graph are displayed on the display 50. The numerical value of the normalized data may be displayed as shown by reference 57.

Furthermore, when the normalized data exceeds a threshold, the data can be displayed by changing the flag character or graph color in an understandable way.

In accordance with the present invention, measured data obtained by analyzing the sample can be displayed by normalizing the measured data for each test result information (a flag or message), it is possible to know the probability that the flag or message can be established. The fact is very useful to establish the need of reexamination and the diagnosis of diseases.

When the normalized data is displayed in a graph, a large amount of information can be grasped at a first glance. Thus, the data can be represented in a more understandable way.

Furthermore, by adding a convertible threshold, reference level for the clinical test can be set based on the experiences and knowledge of the facilities (hospitals and clinical laboratories) and specialists who analyze the test so that the clinical test apparatus can be effectively used.

Still furthermore, the normalized value is useful to know the condition of the sample analyzer. That is, the normalized data can be used as quality control data.

What is claimed is:

1. An apparatus for displaying clinical test result information on blood or urine, comprising:

calculating means for selecting data out of a set of measured data, the measured data being obtained by analyzing blood or urine, in accordance with the clinical test result information to be obtained and normalizing the selected data based upon a predetermined rule;

inputting means for inputting a user-selected threshold level for the clinical test result information; and display means for displaying, as a fraction of a frame, at least one normalized value obtained by the calculating means, the display means further displaying a partition line in the frame as a standard for judging the clinical test result information, the partition line indicating a proportion of the frame, the proportion corresponding to the user-selected threshold level input by the inputting means;

control means for controlling the interaction of the calculating means, the inputting means, and the display means.

2. An apparatus according to claim 1 wherein said calculating means includes a fuzzy reasoning means or a neural network.

3. An apparatus according to claim 2 wherein said calculating means normalizes said selected data based upon the predetermined rule to a value ranging from 0 to 1 using a normalizing function, the normalizing function being adaptively changed by said fuzzy reasoning means or neural network.

4. An apparatus according to claim 1 wherein said display means displays said normalized value as the fraction of the frame together with a border defining said frame and a numerical character indicating said normalized value, and further displaying a predetermined threshold in the form of a partition line on the frame.

5. An apparatus according to claim 4 wherein said display means displays said numerical character and the fraction of the frame by changing the character's color or the fraction's color when the normalized value exceeds the corresponding predetermined threshold.

6. A method for displaying test result information, comprising the steps of:

(a) selecting at least one data from among measured data in accordance with the test result information to be obtained;

(b) normalizing selected data to a value;

(c) inputting a user-selected threshold level for the test result information;

(d) displaying the normalized value as a fraction of a geometric shape, the fraction having a correspondence to the value determined in said step (b); and (e) displaying a partition line for the geometric shape, the partition line indicating a proportion of the geometric shape, the proportion having a correspondence to the user-selected threshold level input in said step (c).

7. The method of claim 6, wherein the normalizing of step (b) includes the sub-steps of:

(b1) selecting a non-linear membership function corresponding to the selected data; and (b2) normalizing the selected data according to the membership function so as to provide the value between zero and one.

8. The method of claim 6, wherein said step (d) further includes the sub-steps of:

(d1) displaying text identifying the selected data; and (d2) displaying in arabic numerals the value determined in said step (b).

9. The method of claim 8, wherein said sub-steps (d1) and (d2) change a display characteristic of the displayed text or arabic numerals, respectively, when the normalized value exceeds the user-selected threshold.

10. The method of claim 9, wherein the display characteristic is color.

11. The method of claim 6, wherein the geometric shape is a rectangular box, and further wherein said step (d) includes:

displaying the borders of the rectangular box; and said step (e) includes:

displaying the partition line as two collinear line segments orthogonal to opposite sides of the rectangular box.

12. The method of claim 6, wherein said step (d) includes changing a display characteristic of the fraction of the geometric shape corresponding to the displayed normalized value when the normalized value exceeds the user-selected threshold of said step (c).

13. The method of claim 6, wherein said step (b) includes the sub-steps of:

(b1) storing at least one normalizing function corresponding to at least one selected data, the normalizing function being used to normalize the selected data to the value between zero and one; and (b2) adaptively changing the normalizing function.

14. The method of claim 6, wherein said step (d) includes:
    displaying the border of the geometric shape; and wherein said step (e) includes:
    displaying the partition line as at least one line segment stretching outside the border of the geometric shape.

15. An apparatus for displaying test result information, comprising:
    a calculator for selecting data out of a set of measured data in accordance with the test result information to be obtained, and normalizing the selected data to a value;
    an input device for inputting a user-selected threshold level for the test result information; and
    a display for displaying the normalized value from said calculator as a fraction of a geometric shape, the fraction being equal to the value determined by said calculator,
    said display also for displaying a partition line for the geometric shape, the partition line indicating a proportion of the geometric shape, the proportion corresponding to the user-selected threshold level input by said input device; and
    a controller for controlling the interaction of said calculator, said input device, and said display.

16. The apparatus of claim 15, further including:
    a memory for storing at least one non-linear normalizing function corresponding to the test result information, wherein said calculator normalizes the selected data according to the corresponding normalizing function so as to provide the value between zero and one.

17. The apparatus of claim 15, said display further displaying text representing the selected data and, in arabic numerals, the value determined by said calculator.

18. The apparatus of claim 17, said display changing a display characteristic of the text or the arabic numeral for the selected data when the normalized value exceeds the user-selected threshold.

19. The apparatus of claim 15, said display further displaying a border of the geometric shape, and displaying the partition line as two collinear line segments orthogonal to opposite borders of the geometric shape.

20. The apparatus of claim 15, said display changing a display characteristic of the fraction of the geometric shape when the normalized value exceeds the user-selected threshold.

21. The apparatus of claim 15, further including:
    a memory for storing at least one membership function corresponding to the test result information, said calculator normalizing the selected data according to the corresponding membership function so as to provide the value between zero and one; and
    fuzzy reasoning means or a neural network for adaptively changing the membership function.

* * * * *